United States Patent
Fukuyama et al.

(10) Patent No.: US 11,498,893 B2
(45) Date of Patent: Nov. 15, 2022

(54) PRODUCTION METHOD FOR CRYSTAL OF REDUCED COENZYME Q10 HAVING EXCELLENT STABILITY

(71) Applicant: KANEKA CORPORATION, Osaka (JP)

(72) Inventors: Yuka Fukuyama, Takasago (JP); Takao Yamaguchi, Takasago (JP)

(73) Assignee: KANEKA CORPORATION, Osaka (JP)

( * ) Notice: Subject to any disclaimer, the term of this patent is extended or adjusted under 35 U.S.C. 154(b) by 0 days.

(21) Appl. No.: 17/280,663

(22) PCT Filed: Sep. 26, 2019

(86) PCT No.: PCT/JP2019/037827
§ 371 (c)(1),
(2) Date: Mar. 26, 2021

(87) PCT Pub. No.: WO2020/067275
PCT Pub. Date: Apr. 2, 2020

(65) Prior Publication Data
US 2021/0355059 A1 Nov. 18, 2021

(30) Foreign Application Priority Data
Sep. 28, 2018 (JP) .............................. JP2018-184620

(51) Int. Cl.
*C07C 46/10* (2006.01)

(52) U.S. Cl.
CPC .......... *C07C 46/10* (2013.01); *C07B 2200/13* (2013.01)

(58) Field of Classification Search
CPC ............................. C07C 46/10; C07B 2200/13
See application file for complete search history.

(56) References Cited

U.S. PATENT DOCUMENTS

| 6,184,255 B1 | 2/2001 | Mae et al. |
| 6,225,474 B1 | 5/2001 | Matsumoto et al. |
| 7,702,534 B1 | 4/2010 | Shimizu |
| 9,388,109 B2 * | 7/2016 | Kawachi .................. A23L 2/52 |
| 9,440,901 B2 * | 9/2016 | Kawachi ................. C07C 41/40 |
| 2014/0120073 A1 | 5/2014 | Kawachi et al. |

FOREIGN PATENT DOCUMENTS

| JP | 10-109933 A | 4/1998 |
| JP | 2003-6409 A | 1/2003 |
| JP | 2003-89669 A | 3/2003 |
| WO | WO 99/65885 A1 | 12/1999 |
| WO | WO 2012/176842 A1 | 12/2012 |

OTHER PUBLICATIONS

International Search Report for PCT/JP2019/037827 dated Nov. 12, 2019.

* cited by examiner

*Primary Examiner* — Sikarl A Witherspoon
(74) *Attorney, Agent, or Firm* — Birch, Stewart, Kolasch & Birch, LLP

(57) ABSTRACT

Provided is a production method capable of efficiently producing a reduced coenzyme Q10 Form II crystal. A method for producing reduced coenzyme Q10 crystals comprises warming a mixture of a reduced coenzyme Q10 Form I crystal and a reduced coenzyme Q10 Form II crystal to 32° C. or higher, in the presence of 0.001 to 50 parts by weight of a solvent with respect to 100 parts by total weight of the crystals, so as to increase the content of the reduced coenzyme Q10 Form II crystal. The warming time may be 1 hour or more and less than 14 hours, and after the warming of the mixture in the presence of the solvent, drying may be performed at 45° C. or higher to remove the solvent.

21 Claims, No Drawings

US 11,498,893 B2

PRODUCTION METHOD FOR CRYSTAL OF REDUCED COENZYME Q10 HAVING EXCELLENT STABILITY

TECHNICAL FIELD

The present invention relates to a method for producing reduced coenzyme Q10 crystals excellent in stability.

BACKGROUND ART

Coenzyme Q is an essential component widely distributed in living organisms from bacteria to mammals, and is known as a member of mitochondrial electron transfer system in cells in the living organisms. Coenzyme Q engages in electron transfer in the electron transfer system by the repetition of oxidation and reduction in mitochondria. Further, reduced coenzyme Q is known to have antioxidant activity. The major component in humans is coenzyme Q10 which is one having 10 repeating structures in the side chain of coenzyme Q, and usually, about 40% to 90% thereof is present in the living body as the reduced form. The physiological activity of coenzyme Q includes activation of energy production by mitochondrial activation, activation of cardiac function, an effect of stabilizing cell membranes, and an effect of protecting cells by antioxidant activity.

While coenzyme Q10 currently produced and sold is, in large part, oxidized coenzyme Q10, reduced coenzyme Q10 which exhibits higher oral absorbability than that of oxidized coenzyme Q10 has also been commercially available and has come to be used in recent years.

A common method for obtaining reduced coenzyme Q10 has already been disclosed (Patent Literature 1). Furthermore, several methods for obtaining reduced coenzyme Q10 as a crystal have also been known. For example, a method of crystallizing reduced coenzyme Q10 in an alcohol solution and/or a ketone solution to produce a crystal (Patent Literature 2), a method of adding a high concentration liquid phase of reduced coenzyme Q10 into a poor solvent for crystallization (Patent Literature 3), and the like have been reported.

On the other hand, Patent Literature 4 reports that crystal polymorphism is found in reduced coenzyme Q10. It also reports that a novel crystal form that is different from those of the above-described publications is obtained. It has been reported that the newly appearing crystal form is much more stable than the conventional reduced coenzyme Q10 and also, is excellent in other physical properties. The method for producing such a novel crystal form of reduced coenzyme Q10 is also disclosed in Patent Literature 4.

Moreover, Patent Literature 5 reports that a carboxylic acid derivative that is totally different from coenzyme Q undergoes a polymorphic change due to solvent-mediated transition.

CITATION LIST

Patent Literature

Patent Literature 1: JP Patent Publication (Kokai) No. 10-109933 A (1998)
Patent Literature 2: JP Patent Publication (Kokai) No. 2003-006409 A
Patent Literature 3: JP Patent Publication (Kokai) No. 2003-089669 A
Patent Literature 4: WO2012-176842
Patent Literature 5: WO1999/065885

SUMMARY OF INVENTION

Technical Problem

Patent Literature 4 discloses a method of obtaining a novel reduced coenzyme Q10 crystal form, namely, a Form II crystal by crystallization or the like. However, as a result of practical studies conducted by the present inventors, it was found that, in the method described in Patent Literature 4, there is a case where it takes a long time to obtain the Form II crystal, or the recovered amount is small, or the content of the Form II crystal in the obtained reduced coenzyme Q10 is low, depending on the conditions of the method. Moreover, Patent Literature 4 discloses, in addition to the crystallization method, a crystal transition method involving addition of shear force and heat. However, this method needs a dedicated special facility, if the method is used in actual production. In particular, since reduced coenzyme Q10 has a relatively low melting point (approximately 50° C.), unless shear force or heat is strictly controlled, the crystal can be melted. Thus, this method is not said to be a highly versatile, simple method.

Under such circumstances, it is an object of the present invention to provide a method for efficiently producing a stable Form II crystal in a short time.

Solution to Problem

As a result of intensive studies directed towards achieving the aforementioned object, the present inventors have found that retaining a mixture of a reduced coenzyme Q10 Form I crystal and a reduced coenzyme Q10 Form II crystal at a predetermined temperature or higher in the presence of a small amount of solvent, can increase the content rate of the reduced coenzyme Q10 Form II crystal. Based on this finding, the present invention has been completed.

Specifically, the present invention relates to a method for producing a reduced coenzyme Q10 Form II crystal, comprising warming a mixture of a reduced coenzyme Q10 Form I crystal and a reduced coenzyme Q10 Form II crystal to 32° C. or higher, in the presence of 0.001 to 50 parts by weight of a solvent with respect to 100 parts by total weight of the crystals, so as to increase the content rate of the reduced coenzyme Q10 Form II crystal. In the above-described method, the warming time is preferably 1 hour or more and less than 14 hours. In addition, in the above-described method, the amount of the reduced coenzyme Q10 Form II crystal to the reduced coenzyme Q10 Form I crystal in the mixture at the initiation of the warming is preferably 1.5 parts by weight or more and 100 parts by weight or less, with respect to 100 parts by weight of the reduced coenzyme Q10 Form I crystal. More preferably, the above-described method further comprises performing drying at 45° C. or higher to remove the solvent, after the warming of the mixture in the presence of the solvent. Furthermore, in the above-described method, the solvent comprises at least one organic solvent selected from the group consisting of a hydrocarbon, an aliphatic acid ester, an ether, an alcohol, a ketone, a nitrogen compound, and a sulfur compound.

The present description encompasses the specification and/or drawings in JP Patent Application No. 2018-184620 which serves as the basis of the priority of the present application.

Advantageous Effects of Invention

The method for producing reduced coenzyme Q10 crystals of the present invention is excellent in that it can produce a reduced coenzyme Q10 Form II crystal that is more stable than the conventionally known reduced coenzyme Q10 Form I crystal in a simple facility in a short time without requiring complicated operations.

DESCRIPTION OF EMBODIMENTS

Hereinafter, the present invention will be described in detail. The "reduced coenzyme Q10" herein may partially include oxidized coenzyme Q10, if it includes reduced coenzyme Q10 as a main component. The "main component" herein means that it is included in a proportion of, for example, 50% by weight or more, usually 60% by weight or more, preferably 70% by weight or more, more preferably 80% by weight or more, further preferably 90% by weight or more, particularly preferably 95% by weight or more, and further particularly preferably 98% by weight or more.

Besides, as mentioned above, the reduced coenzyme Q10 crystal includes two forms of crystal polymorphisms, namely, the conventionally known Form I and a recently newly found Form II. Specifically, the crystal form of reduced coenzyme Q10 having a melting point around 48° C. and showing characteristic peaks at diffraction angles ($2\theta \pm 0.2°$) of 3.1°, 18.7°, 19.0°, 20.2° and 23.0° in powder X-ray (Cu-K$\alpha$) diffraction is Form I, whereas the crystal form of reduced coenzyme Q10 having a melting point around 52° C. and showing characteristic peaks at diffraction angles ($2\theta \pm 0.2°$) of 11.5°, 18.2°, 19.3°, 22.3°, 23.0° and 33.3° in powder X-ray (Cu-K$\alpha$) diffraction is Form II. In the present description, the crystal of reduced coenzyme Q10 that satisfies at least one of the following conditions is referred to as a "reduced coenzyme Q10 Form I crystal": when the temperature is increased at a rate of 5° C./min by differential scanning calorimetry (DSC), the reduced coenzyme Q10 crystal has an endothermic peak at 50±1° C.; when the same measurement is carried out at a temperature rising rate of 0.5° C./min, the reduced coenzyme Q10 crystal has an endothermic peak at 48±1° C.; and in powder X-ray (Cu-K$\alpha$) diffraction, the reduced coenzyme Q10 crystal shows characteristic peaks at diffraction angles ($2\theta \pm 0.2°$) of 3.1°, 18.7°, 19.0°, 20.2°, and 23.0°. Of course, the reduced coenzyme Q10 crystal may satisfy all of said three conditions. On the other hand, the crystal of reduced coenzyme Q10 that satisfies at least one of the following conditions is referred to as a "reduced coenzyme Q10 Form II crystal": when the temperature is increased at a rate of 5° C./min also by differential scanning calorimetry (DSC), the reduced coenzyme Q10 crystal has an endothermic peak at 54±2° C.; when the same measurement is carried out at a temperature rising rate of 0.5° C./min, the reduced coenzyme Q10 crystal has an endothermic peak at 52±2° C.; and in powder X-ray (Cu-K$\alpha$) diffraction, the reduced coenzyme Q10 crystal shows characteristic peaks at diffraction angles ($2\theta \pm 0.2°$) of 11.5°, 18.2°, 19.3°, 22.3°, 23.0°, and 33.3°.

Moreover, the term "crystalline solid" is used in the present description to mean a solid containing therein a portion having a crystal structure and an amorphous portion having no crystal structure.

The method for producing reduced coenzyme Q10 crystals of the present invention comprises warming a mixture of a reduced coenzyme Q10 Form I crystal and a reduced coenzyme Q10 Form II crystal to 32° C. or higher, in the presence of 0.001 to 50 parts by weight of a solvent with respect to 100 parts by total weight of the crystals, so as to increase the content rate of the reduced coenzyme Q10 Form II crystal.

First, a "wet crystal preparation step" of allowing a mixture of a reduced coenzyme Q10 Form I crystal and a reduced coenzyme Q10 Form II crystal to coexist with 0.001 to 50 parts by weight of a solvent with respect to 100 parts by total weight of the crystals will be described.

In the wet crystal preparation step of the present invention, a reduced coenzyme Q10 Form II crystal is allowed to coexist, as a seed crystal for transition, with a reduced coenzyme Q10 Form I crystal. The content rate of the reduced coenzyme Q10 Form II crystal in the mixture is not particularly limited, and it is, for example, 1.5% by weight or more, preferably 2.5% by weight or more, more preferably 5% by weight or more, and particularly preferably 10% by weight or more, with respect to the content of the reduced coenzyme Q10 Form I crystal in the mixture. The upper limit is not particularly limited, and it is generally approximately 100% by weight or less, preferably 50% by weight or less, more preferably 30% by weight or less, and further preferably 20% by weight or less. Moreover, the content rate of the reduced coenzyme Q10 Form II crystal in the mixture is, for example, 1.5% by volume or more, preferably 2.5% by volume or more, more preferably 5% by volume or more, and particularly preferably 10% by volume or more, with respect to the content of the reduced coenzyme Q10 Form I crystal in the mixture. The upper limit is not particularly limited, and it is generally approximately 100% by volume or less, preferably 50% by volume or less, more preferably 30% by volume or less, and further preferably 20% by volume or less. Furthermore, the amount of the reduced coenzyme Q10 Form II crystal in the mixture at the initiation of the warming is, for example, 1.5 parts by weight or more, preferably 2.5 parts by weight or more, more preferably 5 parts by weight or more, and particularly preferably 10 parts by weight or more, with respect to 100 parts by weight of the reduced coenzyme Q10 Form I crystal in the mixture. The upper limit is not particularly limited, and it is generally approximately 100 parts by weight or less, preferably 50 parts by weight or less, more preferably 30 parts by weight or less, and further preferably 20 parts by weight or less.

Besides, the reduced coenzyme Q10 used herein may comprise amorphous-state reduced coenzyme Q10 as a part thereof, as long as it comprises a mixture of a Form I crystal and a Form II crystal as a main component thereof. In addition, since the purity of the reduced coenzyme Q10 can be increased in the after-mentioned warming step, the present reduced coenzyme Q10 may be either reduced coenzyme Q10 having impurities, or unpurified or roughly purified reduced coenzyme Q10 crystals.

In the wet crystal preparation step of the present invention, the solvent used is not particularly limited, and it is preferably a solvent comprising at least one organic solvent selected from the group consisting of a hydrocarbon, an aliphatic acid ester, an ether, an alcohol, a ketone, a nitrogen compound, and a sulfur compound.

Examples of the above-described hydrocarbons include, but are not particularly limited to, aliphatic hydrocarbon, aromatic hydrocarbon, and halogenated hydrocarbon.

The aliphatic hydrocarbon to be used may be cyclic or acyclic, or may be saturated or unsaturated, and is not particularly limited, but is usually one having 3 to 20 carbon atoms, preferably one having 5 to 12 carbon atoms. Specific examples thereof include propane, butane, isobutane, pentane, 2-methylbutane, cyclopentane, 2-pentene, hexane, 2-methylpentane, 2,2-dimethylbutane, 2,3-dimethylbutane, methylcyclopentane, cyclohexane, 1-hexene, cyclohexene, heptane, 2-methylhexane, 3-methylhexane, 2,3-dimethylpentane, 2,4-dimethylpentane, methylcyclohexane, 1-heptene, octane, 2,2,3-trimethylpentane, isooctane, ethylcyclohexane, 1-octene, nonane, 2,2,5-trimethylhexane, 1-nonene, decane, 1-decene, p-menthane, undecane and dodecane. The aliphatic hydrocarbon is preferably pentane, 2-methylbutane, hexane, 2-methylpentane, 2,2-dimethylbutane, 2,3-dimethylbutane, heptane, 2-methylhexane, 3-methylhexane, 2,3-dimethylpentane, 2,4-dimethylpentane, octane, 2,2,3-trimethylpentane, isooctane, nonane, 2,2,5-trimethylhexane, decane, dodecane, cyclopentane, methylcyclopentane, cyclohexane, methylcyclohexane, ethylcyclohexane, and p-menthane. The aliphatic hydrocarbon is more preferably pentane, 2-methylbutane, hexane, 2-methylpentane, 2,2-dimethylbutane, 2,3-dimethylbutane, heptane, 2-methylhexane, 3-methylhexane, 2,3-dimethylpentane, 2,4-dimethylpentane, octane, 2,2,3-trimethylpentane, isooctane, cyclopentane, methylcyclopentane, cyclohexane, methylcyclohexane, and ethylcyclohexane. The aliphatic hydrocarbon is further preferably pentane, hexane, cyclohexane, methylcyclohexane or the like, is particularly preferably heptane, hexane or methylcyclohexane, and is most preferably heptane or hexane.

The aromatic hydrocarbon to be used is not particularly limited, but is usually one having 6 to 20 carbon atoms, preferably one having 6 to 12 carbon atoms, and more preferably one having 7 to 10 carbon atoms. Specific examples thereof include benzene, toluene, xylene, o-xylene, m-xylene, p-xylene, ethylbenzene, cumene, mesitylene, tetralin, butylbenzene, p-cymene, cyclohexylbenzene, diethylbenzene, pentylbenzene, dipentylbenzene, dodecylbenzene and styrene.

The halogenated hydrocarbon to be used may be cyclic or acyclic, or may be saturated or unsaturated, and is not particularly limited, but is preferably acyclic one. The halogenated hydrocarbon is more preferably chlorinated hydrocarbon or fluorinated hydrocarbon, and is further preferably chlorinated hydrocarbon.

In addition, the halogenated hydrocarbon to be used may be one having 1 to 6 carbon atoms, preferably one having 1 to 4 carbon atoms, more preferably one having 1 or 2 carbon atoms. Specific examples thereof include dichloromethane, chloroform, carbon tetrachloride, 1,1-dichloroethane, 1,2-dichloroethane, 1,1,1-trichloroethane, 1,1,2-trichloroethane, 1,1,1,2-tetrachloroethane, 1,1,2,2-tetrachloroethane, pentachloroethane, hexachloroethane, 1,1-dichloroethylene, 1,2-dichloroethylene, trichloroethylene, tetrachloroethylene, 1,2-dichloropropane, 1,2,3-trichloropropane, chlorobenzene and 1,1,1,2-tetrafluoroethane.

Among the above-described hydrocarbons, a hydrocarbon having 5 to 12 carbon atoms is preferable, heptane and hexane are more preferable, and hexane is most preferable.

Examples of the above-described aliphatic acid esters include, but are not particularly limited to, propionic acid ester, acetic acid ester, and formic acid ester. The aliphatic acid ester is preferably acetic acid ester or formic acid ester, and is more preferably acetic acid ester.

Examples of the ester group of the above-described aliphatic acid ester include, but are not particularly limited to, an alkyl ester having 1 to 8 carbon atoms and an aralkyl ester having 1 to 8 carbon atoms. The ester group is preferably an alkyl ester having 1 to 6 carbon atoms and is more preferably an alkyl ester having 1 to 4 carbon atoms.

Examples of the propionic acid ester include methyl propionate, ethyl propionate, butyl propionate, and isopentyl propionate.

Examples of the acetic acid ester include methyl acetate, ethyl acetate, propyl acetate, isopropyl acetate, butyl acetate, isobutyl acetate, sec-butyl acetate, pentyl acetate, isopentyl acetate, sec-hexyl acetate, cyclohexyl acetate, and benzyl acetate. Preferred examples of the acetic acid ester include methyl acetate, ethyl acetate, propyl acetate, isopropyl acetate, butyl acetate, and isobutyl acetate. Most preferred is ethyl acetate.

Examples of the formic acid ester include methyl formate, ethyl formate, propyl formate, isopropyl formate, butyl formate, isobutyl formate, sec-butyl formate, and pentyl formate.

The above-described ether may be cyclic or acyclic, or may be saturated or unsaturated, and is not particularly limited. An ether having generally 3 to 20 carbon atoms, preferably 4 to 12 carbon atoms, and more preferably 4 to 8 carbon atoms may be used.

Specific examples of the ethers include diethyl ether, methyl tert-butyl ether, dipropyl ether, diisopropyl ether, dibutyl ether, dihexyl ether, ethylvinyl ether, butylvinyl ether, anisole, phenetole, butylphenyl ether, methoxytoluene, dioxane, furan, 2-methylfuran, tetrahydrofuran, tetrahydropyran, ethylene glycol dimethyl ether, ethylene glycol diethyl ether, ethylene glycol dibutyl ether, ethylene glycol monomethyl ether, ethylene glycol monoethyl ether, and ethylene glycol monobutyl ether.

The above-described alcohol may be cyclic or acyclic, or may be saturated or unsaturated, and is not particularly limited, but a saturated alcohol is preferably used. An example of the alcohol is a monohydric alcohol having 1 to 20 carbon atoms, and it is preferably one having 1 to 12 carbon atoms, more preferably one having 1 to 6 carbon atoms, further preferably one having 1 to 5 carbon atoms, particularly preferably one having 1 to 4 carbon atoms, and further particularly preferably one having 1 to 3 carbon atoms. The alcohol is most preferably a monohydric alcohol having 2 or 3 carbon atoms. Moreover, a dihydric alcohol having 2 to 5 carbon atoms, preferably 2 or 3 carbon atoms, a trihydric alcohol having 3 carbon atoms, and the like are also preferably used. Among the above-described alcohols, the monohydric alcohol having 1 to 5 carbon atoms has high compatibility with water, and thus, it is preferably used as a mixed solvent with water.

Examples of the monohydric alcohols include methanol, ethanol, 1-propanol, 2-propanol, 1-butanol, 2-butanol, isobutyl alcohol, tert-butyl alcohol, 1-pentanol, 2-pentanol, 3-pentanol, 2-methyl-1-butanol, isopentyl alcohol, tert-pentyl alcohol, 3-methyl-2-butanol, neopentyl alcohol, 1-hexanol, 2-methyl-1-pentanol, 4-methyl-2-pentanol, 2-ethyl-1-butanol, 1-heptanol, 2-heptanol, 3-heptanol, 1-octanol, 2-octanol, 2-ethyl-1-hexanol, 1-nonanol, 1-decanol, 1-undecanol, 1-dodecanol, allyl alcohol, propargyl alcohol, benzyl alcohol, cyclohexanol, 1-methylcyclohexanol, 2-methylcyclohexanol, 3-methylcyclohexanol, and 4-methylcyclohexanol.

Examples of the dihydric alcohols include 1,2-ethanediol, 1,2-propanediol, 1,3-propanediol, 1,2-butanediol, 1,3-butanediol, 1,4-butanediol, 2,3-butanediol, and 1,5-pentanediol.

The trihydric alcohol is, for example, glycerin.

Among the above-described alcohols, a monohydric alcohol having 1 to 5 carbon atoms is preferable, ethanol and propanol are more preferable, and ethanol is most preferable.

The above-described ketones are not particularly limited, and those having 3 to 6 carbon atoms are preferably used. Specific examples of the ketones include acetone, methyl ethyl ketone, methyl butyl ketone, and methyl isobutyl ketone.

Among the above-described ketones, ketone having 3 to 6 carbon atoms is preferable, and acetone is more preferable.

As the above-described nitrogen compounds, for example, nitriles can be used. The nitriles may be cyclic or acyclic, or may be saturated or unsaturated, and is not particularly limited, but saturated nitriles are preferably used. As such nitriles, nitriles having generally 2 to 20 carbon atoms, preferably 2 to 12 carbon atoms, and more preferably 2 to 8 carbon atoms may be used.

Specific examples of the nitriles include acetonitrile, propionitrile, malononitrile, butyronitrile, isobutyronitrile, succinonitrile, valeronitrile, glutaronitrile, hexanenitrile, heptylcyanide, octylcyanide, undecanenitrile, dodecanenitrile, tridecanenitrile, pentadecanenitrile, stearonitrile, chloroacetonitrile, bromoacetonitrile, chloropropionitrile, bromopropionitrile, methoxyacetonitrile, methyl cyanoacetate, ethyl cyanoacetate, tolunitrile, benzonitrile, chlorobenzonitrile, bromobenzonitrile, cyanobenzoic acid, nitrobenzonitrile, anisonitrile, phthalonitrile, bromotolunitrile, methylcyanobenzoate, methoxybenzonitrile, acetylbenzonitrile, naphthonitrile, biphenylcarbonitrile, phenylpropionitrile, phenylbutyronitrile, methylphenylacetonitrile, diphenylacetonitrile, naphthylacetonitrile, nitrophenylacetonitrile, chlorobenzylcyanide, cyclopropanecarbonitrile, cyclohexanecarbonitrile, cycloheptanecarbonitrile, phenylcyclohexanecarbonitrile, and tolylcyclohexanecarbonitrile. Preferred examples of the nitriles include acetonitrile, propionitrile, succinonitrile, butyronitrile, isobutyronitrile, valeronitrile, methyl cyanoacetate, ethyl cyanoacetate, benzonitrile, tolunitrile, and chloropropionitrile; more preferred examples thereof include acetonitrile, propionitrile, butyronitrile, and isobutyronitrile; and the nitrile is most preferably acetonitrile.

Examples of the nitrogen compounds other than the above-described nitriles include nitromethane, triethylamine, pyridine, formamide, N-methylformamide, N,N-dimethylformamide, N,N-dimethylacetamide, and N-methylpyrrolidone.

Examples of the above-described sulfur compounds include dimethyl sulfoxide and sulfolane.

Among the above-described organic solvents, alcohol or aliphatic acid ester is preferable, and ethanol is most preferable.

In the wet crystal preparation step of the present invention, as solvents to be allowed to coexist with the reduced coenzyme Q10 crystal, the above exemplified solvents may be used alone. Otherwise, in order to improve conditions which affect transition conditions, such as the solubility, transition speed, transition rate, and crystallinity of the reduced coenzyme Q10, two or more types of the solvents may be used with being mixed in a preferable proportion according to the properties of each solvent. Alternatively, the above-described organic solvent may also be used in combination with another organic solvent or water. When water is used in combination with the present organic solvent, the wet crystal preparation step can be preferably carried out if the percentage of the organic solvent is relatively high. The percentage of water is preferably 40% by volume or less, more preferably 30% by volume or less, and most preferably 10% by volume or less, with respect to the total volume of the used solvent. The organic solvent used in combination with water is not particularly limited. Ethanol or ethyl acetate is preferable, and ethanol is most preferable.

In the wet crystal preparation step of the present invention, the content of the solvent in wet crystals needs to be 0.001 to 50 parts by weight, with respect to 100 parts by total weight of the crystals. The content of the solvent is not particularly limited, as long as it is with the aforementioned range. The lower limit value is preferably 0.01 part by weight or more, more preferably 0.1 part by weight or more, and further preferably 1 part by weight or more. The upper limit of the content of the solvent in wet crystals depends on the type of the solvent used, and for example, the upper limit of the content of the solvent is preferably 45 parts by weight or less, and more preferably 40 parts by weight or less. Besides, the wet crystal preparation step of the present invention requires that the used reduced coenzyme Q10 crystals are not completely dissolved in the solvent. Specifically, in the wet crystal preparation step of the present invention, a majority of the used reduced coenzyme Q10 crystals need to be maintained in a solid state, or the used reduced coenzyme Q10 crystals need to be in a solid-liquid two-phase system such as a slurry state. Hence, when a solvent having high dissolving ability on reduced coenzyme Q10 is used, the amount of the solvent used may be suppressed, so that the reduced coenzyme Q10 crystals are not completely dissolved in the solvent. Of course, a part of the reduced coenzyme Q10 crystals may be dissolved in the solvent.

In the wet crystal preparation step of the present invention, the method of preparing wet crystals is not particularly limited. Simply, a solvent may be added in a predetermined amount to a mixture of a reduced coenzyme Q10 Form I crystal and a reduced coenzyme Q10 Form II crystal, and then, a mixing operation such as stirring or flowing may be performed on the obtained mixture. Otherwise, a reduced coenzyme Q10 Form I crystal and a solvent may be mixed with each other in predetermined amounts, and then, a reduced coenzyme Q10 Form II crystal may be added to the obtained mixture. Alternatively, a slurry comprising a mixture of a reduced coenzyme Q10 Form I crystal and a reduced coenzyme Q10 Form II crystal may be prepared, and thereafter, in order to set the content of the solvent in wet crystals to be within the above-described range, the slurry may be filtrated to remove an excessive solvent. When the slurry is filtrated, for example, vacuum filtration, pressure filtration or the like can be used. In all cases, it is preferable to adjust so that the used solvent is contacted with the entire reduced coenzyme Q10 crystal.

Subsequently, in the production method of the present invention, a warming step is carried out. In the warming step, the wet crystals of the reduced coenzyme Q10 obtained in the above-described wet crystal preparation step are warmed to 32° C. or higher, so that the content rate of the reduced coenzyme Q10 Form II crystal is increased.

The warming time applied in the above-described warming step is not particularly limited, and it can be adjusted, as appropriate, such that the percentage of the reduced coenzyme Q10 Form II crystal becomes a desired value. The warming time is, for example, 1 hour or more, preferably 2 hours or more, more preferably 4 hours or more, and further preferably 6 hours or more. The upper limit is not particularly limited, either. From the viewpoint of productivity, particularly when the warming step is carried out in an industrial scale, the warming time is preferably not too long, and for example, it is preferably less than 14 hours, and is more preferably 12 hours or less.

In the warming step of the present invention, wet crystals of the reduced coenzyme Q10 may be warmed, either in a mixed state as a result of the stirring, or in a static state. The wet crystals are preferably warmed in a static state.

The temperature applied in the warming step of the present invention is not particularly limited, as long as it is 32° C. or higher. Optimal temperature conditions are different even depending on the type of the used solvent or whether or not the solvent contains water, and thus, the conditions cannot be univocally determined. For example, when only ethanol is used as a solvent, the warming step is carried out at a temperature of preferably 41° C. or lower, and more preferably 40° C. or lower. If the warming temperature is too high, the crystals may be dissolved in some cases. On the other hand, when ethanol containing water is used as a solvent, if the ratio of ethanol/water in the solution (volume ratio) is, for example, larger than 0/1 (volume ratio) and 1/1 (volume ratio) or less, the upper limit of the warming temperature is preferably 47° C. or lower. If the ratio of ethanol/water in the solution is larger than 1/1 (volume ratio) and 3/1 (volume ratio) or less, the upper limit of the warming temperature is preferably 46° C. or lower. If the ratio of ethanol/water in the solution is larger than 3/1 (volume ratio) and 9/1 (volume ratio) or less, the upper limit of the warming temperature is preferably 43° C. or lower. If the ratio of ethanol/water in the solution is larger than 9/1 (volume ratio), the warming step is preferably carried out at a warming temperature of preferably 41° C. or lower, and more preferably 40° C. or lower.

The lower limit of the warming temperature in the warming step of the present invention is 32° C. or higher. From the viewpoint of transition time, the warming step can be preferably carried out at a warming temperature of preferably 35° C. or higher, and more preferably 37° C. or higher.

The apparatus used for warming in the warming step of the present invention is not particularly limited, and examples of the apparatus include a water bath, a Nowter dryer, a conical dryer, and a tray dryer. From the viewpoint of prevention of evaporation of the solvent in the warming step, an apparatus capable of warming in a hermetically sealed state is preferable.

In the production method of the present invention, as described above, the warming step is carried out after completion of the wet crystal preparation step, so that the object can be achieved. However, after completion of the warming step, a step of performing drying at 45° C. or higher to remove the solvent (drying step) may be further carried out, so that the percentage of the reduced coenzyme Q10 Form II crystal can be further enhanced.

In the above-described drying step, the reduced coenzyme Q10 crystals may be dried in a state in which they are mixed by stirring, or may also be dried in a static state. The reduced coenzyme Q10 crystals are preferably dried in a static state.

At the initiation of the drying step, the crystal mixture, in which the percentage of the reduced coenzyme Q10 Form II crystal can be enhanced by the warming step to preferably 50% or more, more preferably 70% or more, further preferably 80% or more, and particularly preferably 90% or more, may be subjected to the present drying step. This percentage can be obtained by the DSC measurement described in Examples. Besides, the percentage of the reduced coenzyme Q10 Form II crystal in the above-described crystal mixture may be expressed with "% by weight" or "% by volume."

The upper limit of the warming temperature in the drying step of the present invention is generally a temperature at which crystals are not melted, and it is preferably 51° C. or lower, and more preferably 50° C. or lower. Regarding the lower limit of the warming temperature from the viewpoint of transition time, the drying step is carried out at a warming temperature of 45° C. or higher, preferably 47° C. or higher, and more preferably 49° C. or higher.

In the drying step of the present invention, the specific surface area is not particularly limited, and it is preferably relatively high. Taking into consideration the warming time from the viewpoint of productivity, the specific surface area is preferably 0.47 or more, and more preferably 1.5 or more. The term "specific surface area" is used herein to mean the surface area per unit volume of a reduced coenzyme Q10 crystal mixture to be subjected to the drying step, and it is indicated by surface area/volume.

Besides, when the desired content rate of the reduced coenzyme Q10 Form II crystal has already been achieved in the warming step, the aforementioned drying conditions shall not apply, and the drying may be carried out at a temperature of, for example, 25° C. or higher, preferably 30° C. or higher, and more preferably 35° C. or higher. The solvent can be removed by performing ordinary drying.

Besides, individual steps in the production method of the present invention, specifically, the above-described wet crystal preparation step, warming step, drying step, and other post-treatment steps, may each be performed under a deoxygenated atmosphere, so that antioxidant effects can be preferably enhanced. The deoxygenated atmosphere can be achieved by the replacement of the atmosphere with an inert gas, reduction of the pressure, boiling, or a combination thereof. The replacement of the atmosphere with an inert gas, namely, an inert gas atmosphere is preferably used. Examples of the above-described inert gas include nitrogen gas, helium gas, argon gas, hydrogen gas, and carbon dioxide, and preferred is nitrogen gas. According to the present invention, reduced coenzyme Q10 crystals with high quality can be obtained with good workability and good economic efficiency. For example, wet crystals prepared in the wet crystal preparation step (a combination of a mixture of a reduced coenzyme Q10 Form I crystal and a reduced coenzyme Q10 Form II crystal, with a solvent) is placed in a vessel, and the gas phase in the vessel is replaced with an inert gas. Thereafter, the vessel is hermetically closed, and a warming step is then performed by warming the wet crystals in the vessel. This is one example of performing a warming step under a deoxygenated atmosphere.

The content rate of the reduced coenzyme Q10 Form II crystal in the reduced coenzyme Q10 crystals or the crystalline solids, which are obtained after completion of each step or are finally obtained, can be determined by measuring with, for example, a differential scanning calorimeter (DSC).

As mentioned above, when the reduced coenzyme Q10 Form II crystal is measured with DSC at a temperature rising rate of 0.5° C./min, it exhibits an endothermic peak around 52±2° C. On the other hand, the conventional reduced coenzyme Q10 Form I crystal exhibits an endothermic peak around 48±1° C. under the same conditions as those described above. Even in a state in which the reduced coenzyme Q10 Form II crystal is mixed with the conventional reduced coenzyme Q10 Form I crystal or a crystalline solid thereof, the content rate of the reduced coenzyme Q10 Form II crystal can be determined based on the height of the endothermic peak, or the ratio of the endothermic amount.

EXAMPLES

Hereinafter, the present invention will be more specifically described with reference to Examples. However, the technical scope of the present invention is not intended to be limited to these Examples. It is to be noted that the measurement conditions of DSC in Examples and Comparative Examples are as follows.

(DSC Measurement Conditions)
Apparatus: DSC 6220, manufactured by SII Nano Technology Inc.
Sample container: Aluminum pan & cover (SSC000C008)
Rate of temperature rise: 0.5° C./min
Amount of sample: 5±2 mg From the height (Difference Y) of the endothermic peak of a reduced coenzyme Q10 Form I crystal obtained by DSC analysis (hereinafter referred to as "Difference I-Y") and the height (Difference Y) of the endothermic peak of a reduced coenzyme Q10 Form II crystal obtained by DSC analysis (hereinafter referred to as "Difference II-Y"), the percentage of the reduced coenzyme Q10 Form II crystal (Form II rate) was calculated as follows.

$$\text{Form II rate}(\%) = \frac{(\text{Difference II} - Y)}{(\text{Difference I} - Y) + (\text{Difference II} - Y)} \times 100$$

Example 1

5.0 g of a reduced coenzyme Q10 Form I crystal, 49 mL of ethanol, and 16 mL of distilled water were mixed with one another to prepare a slurry. Thereafter, 0.125 g of a reduced coenzyme Q10 Form II crystal that corresponded to 2.5 parts by weight with respect to 100 parts by weight of the reduced coenzyme Q10 Form I crystal was added to the slurry, followed by stirring. The resultant slurry was filtrated under reduced pressure, so that the ratio of the solvent with respect to 100 parts by total weight of the crystals was set to be 27 parts by weight. The obtained wet crystals were added into a vial, and nitrogen was then blown into the vial, followed by hermetically sealing. These wet crystals were placed in a 44° C. water bath, and were then warmed for 8 hours. After completion of the warming, the resultant was dried under reduced pressure (35° C.) to obtain dry crystals. The percentage of the reduced coenzyme Q10 Form II crystal in the obtained dry crystals was 63.7%.

Example 2

5.0 g of a reduced coenzyme Q10 Form I crystal, 33 mL of ethanol, 33 mL of distilled water were mixed with one another to prepare a slurry. Thereafter, 0.125 g of a reduced coenzyme Q10 Form II crystal that corresponded to 2.5 parts by weight with respect to 100 parts by weight of the reduced coenzyme Q10 Form I crystal was added to the slurry, followed by stirring. The resultant slurry was filtrated under reduced pressure, so that the ratio of the solvent with respect to 100 parts by total weight of the crystals was set to be 27 parts by weight. The obtained wet crystals were added into a vial, and nitrogen was then blown into the vial, followed by hermetically sealing. These wet crystals were placed in a 45.5° C. water bath, and were then warmed for 8 hours. After completion of the warming, the resultant was dried under reduced pressure (35° C.) to obtain dry crystals. The percentage of the reduced coenzyme Q10 Form II crystal in the obtained dry crystals was 24.1%.

Example 3

2.0 g of a reduced coenzyme Q10 Form I crystal was mixed with 26 mL of ethanol to prepare a slurry. Thereafter, 0.03 g of a reduced coenzyme Q10 Form II crystal that corresponded to 1.5 parts by weight with respect to 100 parts by weight of the reduced coenzyme Q10 Form I crystal was added to the slurry, followed by stirring. The resultant slurry was filtrated under reduced pressure up to the same level as that of Example 1 (the ratio of the solvent was approximately 30 parts by weight with respect to 100 parts by total weight of the crystals). The obtained wet crystals were added into a vial, and nitrogen was then blown into the vial, followed by hermetically sealing. These wet crystals were placed in a 37° C. water bath, and were then warmed for 10 hours.

After completion of the warming, the resultant was dried under reduced pressure (35° C.) to obtain dry crystals. The percentage of the reduced coenzyme Q10 Form II crystal in the obtained dry crystals was 80.3%.

Example 4

2.0 g of a reduced coenzyme Q10 Form I crystal was mixed with 26 mL of ethanol to prepare a slurry. Thereafter, 0.02 g of a reduced coenzyme Q10 Form II crystal that corresponded to 1 part by weight with respect to 100 parts by weight of the reduced coenzyme Q10 Form I crystal was added to the slurry, followed by stirring. The resultant slurry was filtrated under reduced pressure up to the same level as that of Example 1 (the ratio of the solvent was approximately 30 parts by weight with respect to 100 parts by total weight of the crystals). The obtained wet crystals were added into a vial, and nitrogen was then blown into the vial, followed by hermetically sealing. These wet crystals were placed in a 37° C. water bath, and were then warmed for 10 hours. After completion of the warming, the resultant was dried under reduced pressure (35° C.) to obtain dry crystals. The percentage of the reduced coenzyme Q10 Form II crystal in the obtained dry crystals was 34.6%.

Example 5

5.0 g of a reduced coenzyme Q10 Form I crystal was mixed with 65 mL of ethanol to prepare a slurry. Thereafter, 0.25 g of a reduced coenzyme Q10 Form II crystal that corresponded to 5 parts by weight with respect to 100 parts by weight of the reduced coenzyme Q10 Form I crystal was added to the slurry, followed by stirring. The resultant slurry was filtrated under reduced pressure, so that the ratio of the solvent with respect to 100 parts by total weight of the crystals was set to be 34 parts by weight. The obtained wet crystals were added into a vial, and nitrogen was then blown into the vial, followed by hermetically sealing. These wet crystals were placed in a 40° C. water bath, and were then warmed for 6 hours. After completion of the warming, the resultant was dried under reduced pressure (35° C.) to obtain dry crystals. The percentage of the reduced coenzyme Q10 Form II crystal in the obtained dry crystals was 100%.

Example 6

1.0 g of a reduced coenzyme Q10 Form I crystal was mixed with 20 mL of ethanol to prepare a slurry. Thereafter, 1.0 g of a reduced coenzyme Q10 Form II crystal that corresponded to 100 parts by weight with respect to 100 parts by weight of the reduced coenzyme Q10 Form I crystal 100 parts by weight was added to the slurry, followed by stirring. The resultant slurry was filtrated under reduced pressure up to the same level as that of Example 1 (the ratio of the solvent was approximately 30 parts by weight with respect to 100 parts by total weight of the crystals). The obtained wet crystals were added into a vial, and nitrogen was then blown into the vial, followed by hermetically sealing. These wet crystals were placed in a 32° C. water bath, and were then warmed for 14 hours. After completion of the warming, the resultant was dried under reduced pressure (35° C.) to obtain dry crystals. The percentage of the reduced coenzyme Q10 Form II crystal in the obtained dry crystals was 90.9%.

Comparative Example 1

1.0 g of a reduced coenzyme Q10 Form I crystal was mixed with 30 mL of ethanol to prepare a slurry. Thereafter, 1.0 g of a reduced coenzyme Q10 Form II that corresponded to 100 parts by weight with respect to 100 parts by weight of the reduced coenzyme Q10 Form I crystal was added to the slurry, followed by stirring. The resultant slurry was filtrated under reduced pressure up to the same level as that of Example 1 (the ratio of the solvent was approximately 30 parts by weight with respect to 100 parts by total weight of the crystals). The obtained wet crystals were added into a vial, and nitrogen was then blown into the vial, followed by hermetically sealing. These wet crystals were placed in a 30° C. water bath, and were then warmed for 14 hours. After completion of the warming, the resultant was dried under reduced pressure (35° C.) to obtain dry crystals. The percentage of the reduced coenzyme Q10 Form II crystal in the obtained dry crystals was 59.2%, and thus, almost no increase in the percentage of the Form II crystal was observed.

Example 7

1.4 g of a reduced coenzyme Q10 Form I crystal was mixed with 29 mL of ethanol to prepare a slurry. Thereafter, 0.1 g of a reduced coenzyme Q10 Form II crystal was added to the slurry. The resultant slurry was filtrated under reduced pressure, so that the ratio of the solvent with respect to 100 parts by total weight of the crystals was set to be 46 parts by weight, thereby obtaining wet crystals. The obtained wet crystals were added into a vial, and nitrogen was then blown into the vial, followed by hermetically sealing. These wet crystals were placed in a 37° C. water bath, and were then warmed for 4 hours. Thereafter, the resultant was dried under reduced pressure (35° C.), and was then dried using a vacuum dryer at 45° C. for 8 hours. The percentage of the reduced coenzyme Q10 Form II crystal in the obtained dry crystals was 94.6%. Moreover, after completion of the warming step, wet crystals before drying were sampled, and the percentage of the reduced coenzyme Q10 Form II crystal in the wet crystals was measured. As a result, the percentage of the reduced coenzyme Q10 Form II crystal was 60.2%.

Example 8

1.6 g of a reduced coenzyme Q10 Form I crystal was mixed with 13 mL of ethanol to prepare a slurry. Thereafter, 0.16 g of a reduced coenzyme Q10 Form II crystal that corresponded to 10 parts by weight with respect to 100 parts by weight of the reduced coenzyme Q10 Form I crystal was added to the slurry, followed by stirring. The resultant slurry was filtrated under reduced pressure, so that the ratio of the solvent with respect to 100 parts by total weight of the crystals was set to be 38 parts by weight. The obtained wet crystals were added into a vial, and nitrogen was then blown into the vial, followed by hermetically sealing. These wet crystals were placed in a 37° C. water bath, and were then warmed for 6 hours. After completion of the warming, the resultant was dried under reduced pressure (35° C.), and was further warmed using a vacuum dryer at 45° C. for 8 hours. The percentage of the reduced coenzyme Q10 Form II crystal in the obtained dried crystals was 100%. Moreover, after completion of the warming step, wet crystals before drying were sampled, and the percentage of the reduced coenzyme Q10 Form II crystal in the wet crystals was measured. As a result, the percentage of the reduced coenzyme Q10 Form II crystal was 89.9%.

Example 9

2 g of a reduced coenzyme Q10 Form I crystal was mixed with acetonitrile to prepare a slurry. Thereafter, 0.25 g of a reduced coenzyme Q10 Form II crystal that corresponded to 12.5 parts by weight with respect to 100 parts by weight of the reduced coenzyme Q10 Form I crystal was added to the slurry, followed by stirring. The resultant slurry was filtrated under reduced pressure up to the same level as that of Example 1 (the ratio of the solvent was approximately 30 parts by weight with respect to 100 parts by total weight of the crystals). The obtained wet crystals were added into a vial, and nitrogen was then blown into the vial, followed by hermetically sealing. These wet crystals were placed in a 37° C. water bath, and were then warmed for 5 hours. After completion of the warming, the resultant was dried under reduced pressure (35° C.) to obtain dry crystals. The percentage of the reduced coenzyme Q10 Form II crystal in the obtained dried crystals was 52.5%.

Example 10

2 g of a reduced coenzyme Q10 Form I crystal was mixed with ethyl acetate containing 2% to 3% water to prepare a slurry. Thereafter, 0.25 g of a reduced coenzyme Q10 Form II crystal that corresponded to 12.5 parts by weight with respect to 100 parts by weight of the reduced coenzyme Q10 Form I crystal was added to the slurry, followed by stirring. The resultant slurry was filtrated under reduced pressure up to the same level as that of Example 1 (the ratio of the solvent was approximately 30 parts by weight with respect to 100 parts by total weight of the crystals). The obtained wet crystals were added into a vial, and nitrogen was then blown into the vial, followed by hermetically sealing. These wet crystals were placed in a 36° C. water bath, and were then warmed for 5 hours. After completion of the warming, the resultant was dried under reduced pressure (35° C.) to obtain dry crystals. The percentage of the reduced coenzyme Q10 Form II crystal in the obtained dried crystals was 87.6%.

All publications, patents and patent applications cited in the present description are incorporated herein by reference in their entirety.

The invention claimed is:

1. A method for producing reduced coenzyme Q10 Form II crystals, comprising:
    warming a first mixture of a reduced coenzyme Q10 Form I crystal and a reduced coenzyme Q10 Form II crystal to 32° C. to less than the temperature at which all of the crystals dissolve, in the presence of 0.001 to 50 parts by weight of a solvent with respect to 100 parts by total weight of the crystals to form a second mixture,
    wherein the warming is performed while maintaining the crystals in a wet crystal state, and
    wherein a content of the reduced coenzyme Q10 Form II crystals in the second mixture is increased over the first mixture.

2. The method according to claim 1, wherein the warming time is 1 hour or more and less than 14 hours.

3. The method according to claim 1, wherein an amount of the reduced coenzyme Q10 Form II crystal to the reduced coenzyme Q10 Form I crystal in the mixture at an initiation of the warming is 1.5 parts by weight or more and 100 parts by weight or less, with respect to 100 parts by weight of the reduced coenzyme Q10 Form I crystal in the mixture.

4. The method according to claim 1, further comprising: performing drying at 45° C. or higher to remove the solvent, after the warming of the mixture in the presence of the solvent.

5. The method according to claim 4, wherein the content of the reduced coenzyme Q10 Form II crystal in the mixture at the initiation of the drying is 50% or more.

6. The method according to claim 1, wherein the warming is carried out in a static state.

7. The method according to claim 1, wherein the solvent comprises at least one organic solvent selected from the group consisting of a hydrocarbon, an aliphatic acid ester, an ether, an alcohol, a ketone, a nitrogen compound, and a sulfur compound.

8. The method according to claim 7, wherein the solvent comprises at least a hydrocarbon, which is a hydrocarbon having 5 to 12 carbon atoms.

9. The method according to claim 8, wherein the hydrocarbon having 5 to 12 carbon atoms is hexane.

10. The method according to claim 7, wherein the solvent comprises at least an alcohol, which is a monohydric alcohol having 1 to 5 carbon atoms.

11. The method according to claim 10, wherein the monohydric alcohol having 1 to 5 carbon atoms is ethanol.

12. The method according to claim 7, wherein the solvent comprises at least a ketone, which is a ketone having 3 to 6 carbon atoms.

13. The method according to claim 12, wherein the ketone having 3 to 6 carbon atoms is acetone.

14. The method according to claim 1, which is carried out under a deoxygenated atmosphere.

15. The method according to claim 1, further comprising: performing drying at 25° C. or higher to remove the solvent, after the warming of the mixture in the presence of the solvent.

16. The method according to claim 1, which is carried out on an industrial scale.

17. The method according to claim 16, wherein the warming is carried out for than 12 hours.

18. The method according to claim 4, wherein the content of the reduced coenzyme Q10 Form II crystal in the mixture at the initiation of the drying is 70% or more.

19. The method according to claim 1, wherein the reduced coenzyme Q10 Form II crystal is characterized by powder X-ray (Cu-Kα) diffraction peaks (2θ±) 0.2°) at 11.5°, 18.2°, 19.3°, 22.3°, 23.0° and 33.3°.

20. The method according to claim 1, wherein the reduced coenzyme Q10 Form II crystal is characterized by an endothermic peak around 52±2° C. when measured with DSC at a heating rate of 0.5° C./min or by an endothermic peak around 54±2° C. when measured with DSC at a heating rate of 5° C./min.

21. The method according to claim 1, which comprises warming a first mixture of a reduced coenzyme Q10 Form I crystal and a reduced coenzyme Q10 Form II crystal to 32° C. to 47° C. or lower.

* * * * *